(12) United States Patent
Nordqvist

(10) Patent No.: US 11,426,532 B2
(45) Date of Patent: Aug. 30, 2022

(54) NEEDLE GUARD WITH DUAL HINGE FUNCTIONALITY

(71) Applicant: VIGMED AB, Helsingborg (SE)

(72) Inventor: Anders Nordqvist, Hoganas (SE)

(73) Assignee: Greiner Bio-One GmbH, Kremsmunster (AT)

( * ) Notice: Subject to any disclaimer, the term of this patent is extended or adjusted under 35 U.S.C. 154(b) by 253 days.

(21) Appl. No.: 15/741,092

(22) PCT Filed: Jun. 30, 2016

(86) PCT No.: PCT/SE2016/050662
§ 371 (c)(1),
(2) Date: Dec. 29, 2017

(87) PCT Pub. No.: WO2017/003363
PCT Pub. Date: Jan. 5, 2017

(65) Prior Publication Data
US 2018/0185590 A1 Jul. 5, 2018

(30) Foreign Application Priority Data

Jun. 30, 2015 (SE) .................................... 1550916-9

(51) Int. Cl.
*A61D 7/00* (2006.01)
*A61M 5/32* (2006.01)

(52) U.S. Cl.
CPC .............. *A61M 5/3216* (2013.01); *A61D 7/00* (2013.01); *A61M 2250/00* (2013.01)

(58) Field of Classification Search
CPC ............ A61M 5/3216; A61M 2250/00; A61M 2005/3217; A61M 5/3219; A61M 5/3202; A61M 2005/3246
See application file for complete search history.

(56) References Cited

U.S. PATENT DOCUMENTS 5,151,089 A * 9/1992 Kirk, III ............. A61M 5/3216
604/263
5,242,417 A * 9/1993 Paudler ............... A61M 5/3216
604/263
(Continued)

FOREIGN PATENT DOCUMENTS

CN 101687083 A 3/2010
EP 0489419 A1 6/1992
(Continued)

OTHER PUBLICATIONS

Chinese Search Report for Chinese Patent Application No. 201680038630.5.

*Primary Examiner* — William R Carpenter
*Assistant Examiner* — William R Frehe
(74) *Attorney, Agent, or Firm* — Fishman Stewart PLLC

(57) ABSTRACT

A needle guard for protecting a human or animal from accidental contact with a needle connected to said needle guard is disclosed. The needle guard comprises a mounting base for the needle, a hinge structure connecting the mounting base to a needle shield, and a needle shield hinge adjacent to the hinge structure and needle shield. The hinge structure is adapted to pivot the needle shield relative to the mounting base from an open position in which the needle shield is separated from the needle, to a closed position in which the needle shield encloses the needle. The needle shield hinge is adapted to pivot the needle shield relative to the hinge structure. A method of manufacturing the needle guard is also disclosed.

9 Claims, 3 Drawing Sheets

(56) References Cited

U.S. PATENT DOCUMENTS

| | | | | |
|---|---|---|---|---|
| 5,312,369 A * | 5/1994 | Arcusin | ............... | A61M 5/3216 604/263 |
| 5,885,249 A * | 3/1999 | Irisawa | ............... | A61M 5/3216 604/263 |
| 5,910,130 A * | 6/1999 | Caizza | ................ | A61M 5/3275 604/110 |
| 5,913,846 A * | 6/1999 | Szabo | ................. | A61M 5/3216 128/919 |
| 2005/0054986 A1 * | 3/2005 | Simpson | ............. | A61M 5/3216 29/428 |
| 2008/0208138 A1 * | 8/2008 | Lim | .................... | A61M 5/3216 604/192 |
| 2014/0135713 A1 * | 5/2014 | Domonkos | ........ | A61B 17/3496 29/525 |
| 2014/0296792 A1 * | 10/2014 | Chun | ................. | A61M 5/3275 604/263 |
| 2016/0296712 A1 * | 10/2016 | Minix | ................. | A61M 5/3216 |

FOREIGN PATENT DOCUMENTS

| | | | |
|---|---|---|---|
| SE | 1150633 A1 | 1/2013 | |
| WO | WO-2015097034 A1 | 7/2015 | |

* cited by examiner

NEEDLE GUARD WITH DUAL HINGE FUNCTIONALITY

CROSS-REFERENCE TO RELATED APPLICATIONS

This application claims priority to Swedish Patent Application No. 1550916-9, filed on Jun. 30, 2015, and PCT/SE2016/050662 filed Jun. 30, 2016, the contents of which are hereby incorporated by reference in their entirety.

TECHNICAL FIELD

The present disclosure relates to a needle guard arranged to shield a needle from accidental contact with an animal or human such as patients and medical personnel.

BACKGROUND

The clinical utilization of a pointed hollow needle is well known in the medical art for the administration of solutions or suspensions, such as medicaments, to a human or animal. After puncturing of the skin and introduction of the needle tip the content of a syringe typically connected to the rear part of the needle is administered to the human or animal through the hollow needle. The needle has then done its duty and is withdrawn from the human or animal. However, an unprotected withdrawn needle constitutes a serious health hazard due to the fact that it may be contaminated with e.g. infectious agents originating from the patient's blood or other body fluids, in combination with the needle tip's inherent ability to easily penetrate skin. Hence, the medical personnel who are handling the withdrawn needle may acquire an undesirable disease, e.g. HIV or hepatitis, if they accidentally contact the needle with their skin. In order to circumvent or alleviate the health hazards associated with such a withdrawn needle there has been much effort devoted to developing various needle tip protectors.

U.S. Pat. No. 5,603,699 discloses a needle guard assembly comprising a mounting base and a jacket assembly pivotally mounted on the mounting base. The jacket assembly comprises a shield member, a lever member and activating means. The activating means are adapted for movement of the jacket assembly from a retracted position to a closed position around a needle. Disadvantages of this needle guard assembly include its complicated construction and inherent bulkiness. The former being associated with a large cost of production and the latter with at least an increased volume of bio-hazard waste. Furthermore, a multi-part needle guard such as this is associated with a relatively high cost of production and difficulties in its assembly.

EP 0 887 082 A2 describes a safety cover which is pivoting around a point near the needle hub. The safety cover is folded forwards and to the side over the needle after injection and withdrawal of the needle from the skin. To assure sufficient locking force, the pivoting safety cover is provided with a locking hook mechanism that mates with the needle hub upon locking, which in turn demands the manual push of the pivoting safety cover to be sufficient to overcome the resistance of the locking hook mechanism. This force needs to be relatively high, which increases the risk of the user not to lock the safety cover in e.g. a stressful situation. The safety cover may thus be left unlocked which results in a potential health hazard. Also, the needle tip is not secured until the pivoting arm has been manually pushed against the needle shaft, before which the user still is susceptible to stung/cut.

Additional safety covers of the prior art with a construction similar to the construction of the safety cover described in EP 0 887 082 A2, such as the safety cover disclosed in U.S. Pat. No. 4,982,842, may comprise an additional looking hook mechanism that locks around the shaft of the needle, or only a looking hook mechanism that locks around the shaft of the needle. The force needed to overcome the resistance of the locking hook mechanism needs, also in these cases, to be quite high. This force is also applied on the needle. The needle may therefore be broken or lost from the cooperation with the hub. This presents a danger to the user, since the user may be stung or cut on the broken/lost needle.

None of above described needle guards protects the needle immediately after withdrawal of the needle from the skin. Hence, a user may accidently come into contact with the needle tip in the time span between withdrawal of the needle and activation of the needle guard by the user. It is well known that the patient often moves during the painful administration of medicaments through the needle, i.e. when the content of the connected syringe is injected. Such movement by the patient may result in involuntary withdrawal of the needle, leaving it exposed and without protection from accidental contact. It is estimated that 20 to 25% of all accidents in which medical personnel are injured by the needle occur during the actual injection of the syringe content.

WO 2013/006134 discloses a needle guard for shielding of a needle. However, due to its design the needle guard of WO 2013/006134 occupies a large volume when the guard is packaged, transported and stored prior to its use by medical personnel on humans or animals. This increases the costs associated with each of the steps prior to the end use.

It would therefore be desirable to provide a needle guard which addresses the drawbacks associated with the above described needle guards while reducing costs associated with packaging, transporting and storing the needle guard.

SUMMARY

The present disclosure seeks to mitigate, alleviate, circumvent or eliminate at least one of the above identified deficiencies in the art.

Accordingly an aspect disclosed herein relates to a needle guard for protecting a human or animal from accidental contact with a needle connected to said needle guard, comprising:
a mounting base for the needle;
a hinge structure connecting the mounting base to a needle shield, the hinge structure being adapted to pivot the needle shield relative to the mounting base from an open position in which the needle shield is separated from the needle, to a closed position in which the needle shield encloses the needle; and
a needle shield hinge adjacent to the hinge structure and needle shield, the needle shield hinge being adapted to pivot the needle shield relative to the hinge structure.

Further advantageous embodiments are disclosed below and in the appended patent claims.

DETAILED DESCRIPTION

An embodiment of the present disclosure will not be described below with reference to Figs. 1, 2 and 3 in order for those skilled in the art to be able to carry out the disclosure. The disclosure may also be embodied in alternative forms and should not be construed as limited to the embodiment set forth therein. Rather, the embodiment is provided so that this disclosure will be thorough and complete, and will fully convey the scope of the disclosure to those skilled in the art. The disclosure is only limited by appended patent claims. Reference to various features of the drawings is done by numbers according to the table below.

Figure 1:
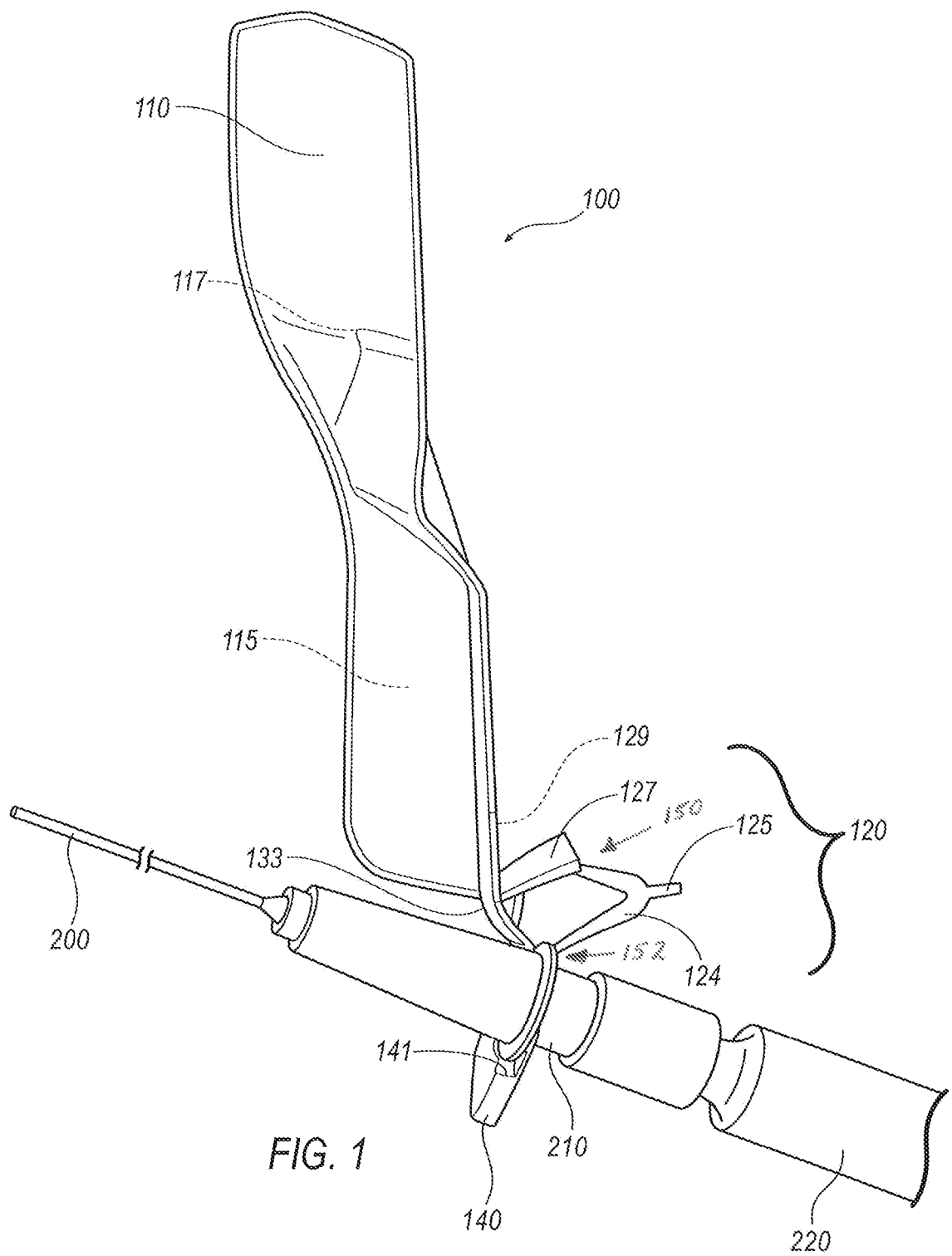
FIG. 1 is a side view of a needle guard in a half-open position according to one embodiment of the disclosure.
Figure 2:
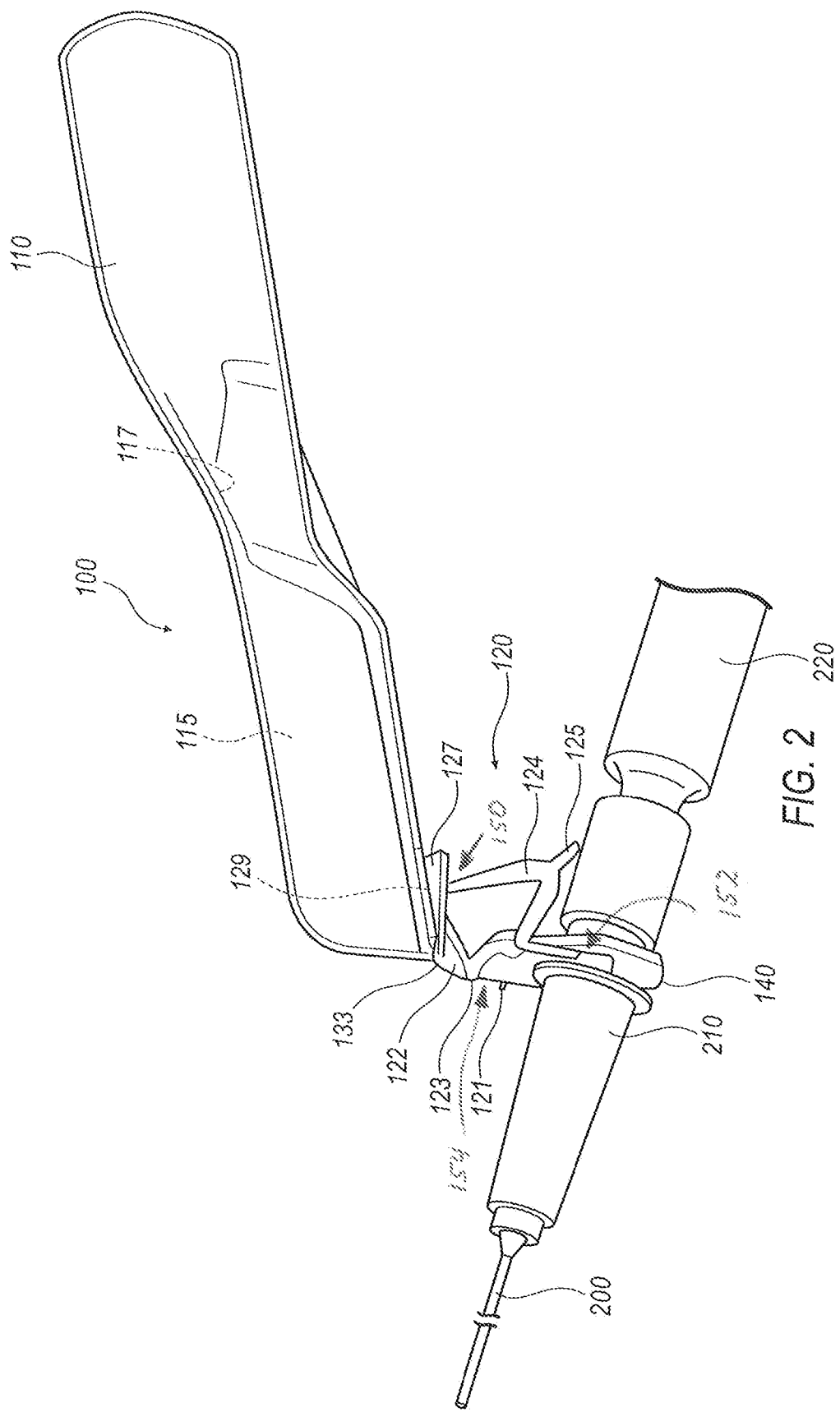
FIG. 2 is the needle guard of FIG. 1 in the open position prior to use.
Figure 3:
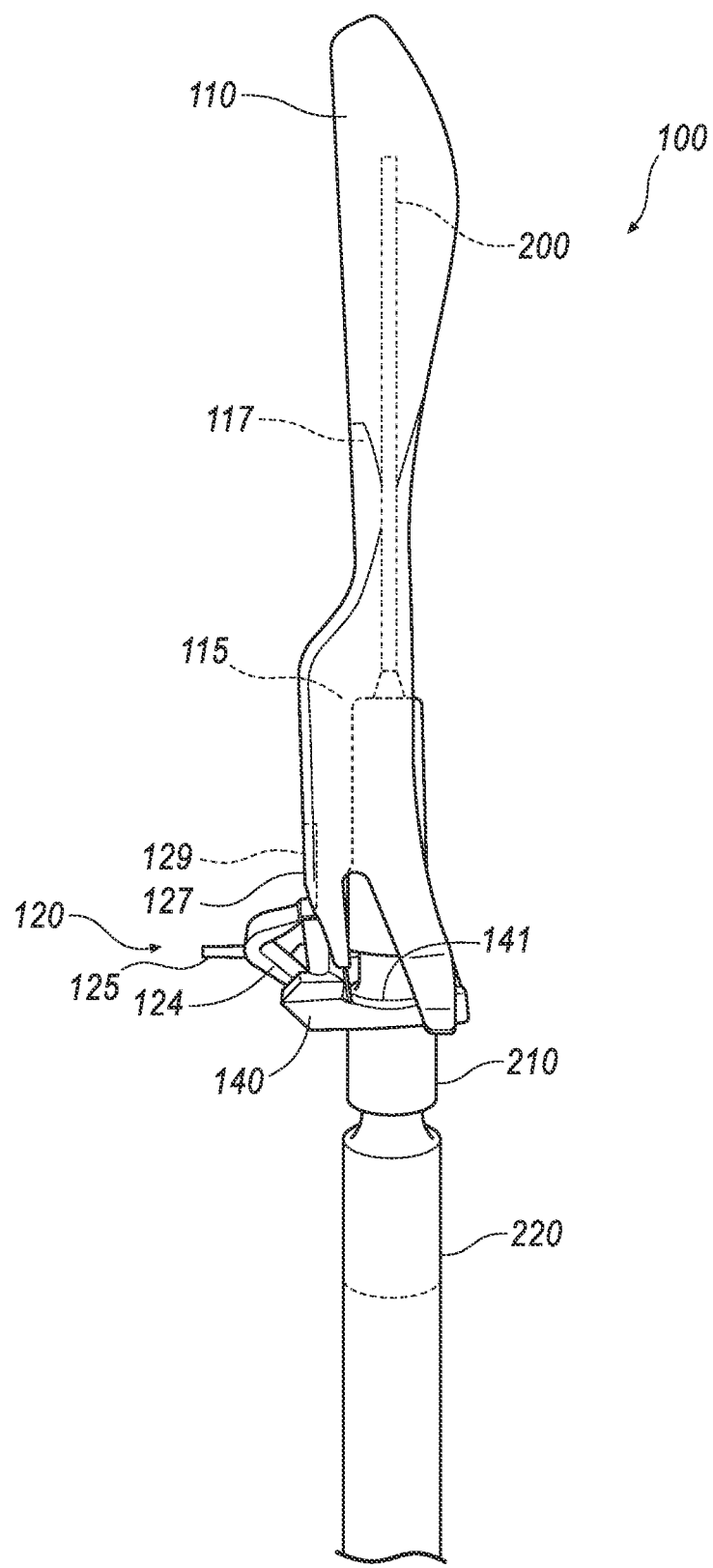
FIG. 3 is a side view of the needle guard of FIG. 1 in the closed position.

Number Feature
100 needle guard
110 needle shield
115 elongated slot
117 needle lock
120 hinge structure
121 toggle joint
122 leg portion
123 toggle joint knee
124 spring member
125 press member
127 spring plate
129 aperture
133 needle shield hinge
140 mounting base
141 needle hub bore Figs. 1, 2, and 3 illustrate a needle guard 100. The needle guard 100 broadly comprises four parts in the form of (i) a needle shield 110, (ii) a hinge structure 120, (iii) a needle shield hinge 133, and (iv) a mounting base 140.

The needle shield 110 may be shaped as a rod, arm or other similar elongated structure that is able to receive and enclose a needle 200 during use as will be described further below. An elongated slot 115 is formed longitudinally on the needle shield 110 for allowing sideways entry and acceptance of the needle 200. The ratio between the width of the elongated slot 115 to the diameter of the needle may be 10 to 1, 5 to 1, or preferably 2 to 1. In use the lower end portion of the needle shield 110 may be in contact with the mounting base 140 such that the entire length of the needle is enclosed by the needle shield 110. The needle shield 110 also comprises a needle lock 117 in the slot 115 which securely engages the needle and therefore the needle shield 110 in the closed position during use so that I may not revert to the open position. The needle lock 117 may comprise one or several locking members extending from or forming a part of the needle shield 110 for example, a hook-shaped extension. If desired, the needle shield 110 may be provided with suitable color indicators correlating with differing needle sizes. The needle shield 110 also comprises an aperture 129 for fixedly receiving a spring plate 127 of the hinge structure 120 during use as will be described below.

The needle shield 110 is connected to the mounting base 140 through hinge structure 120. The hinge structure 120 comprises V-shaped spring member 124 connected to the mounting base 140 and a spring plate 127 connected to the spring member 124. The spring member 124 comprises a press member 125 for applying pressure to the hinge structure 120 by way of a user's finger or thumb during injection of a medicament. As shown in FIG. 2, the hinge structure 120 further comprises a toggle joint 121 adjacent to the mounting base 140, a leg portion 122 adjacent to a needle shield hinge 133, and a toggle joint knee 123 between the toggle joint 121 and the leg portion 122. This arrangement provides for a dead-center toggle function in the hinge structure 120 that forces the needle shield 110 to one of two oppositely-disposed positions being the open position (shown in FIG. 2) or the closed position (shown in FIG. 3). In the open position the needle shield 110 is remotely positioned from the needle 200 on the mounting base 140 so that the needle 200 is exposed and is able to penetrate the skin of a patient. In the closed position the needle 200 is enclosed and protected by the needle shield 110. When a force is applied by a user to the needle shield 110 in a direction from the open position and past the dead-center position, the hinge structure 120 snaps the needle shield 110 into the closed position. The dead-center position of the hinge structure 120 corresponds to a dead-centre angle between the longitudinal extensions of the needle and the needle shield 110. If the angle is less than the dead-centre angle the needle shield 110 strives toward the closed position (FIG. 3) thereby receiving the needle in slot 115. If the angle is greater than the dead-centre angle, the needle shield 110 strives toward the open position (FIG. 2). The dead-centre angle may be in the range of 45 to 170°, such as 80 to 120° or 90 to 110°. A longer leg portion 122 increases the dead-center angle. Moving the point of attachment of spring member 124 further above the point of attachment of the toggle joint 121 decreases the dead-center angle.

A needle shield hinge 133 is located adjacent to needle shield 110 and the leg portion 122 of hinge structure 120. The needle shield hinge 133 permits pivoting of the needle shield 110 relative to the hinge structure 120. This occurs independently from pivoting of the needle shield 110 relative to the mounting base 140 between open and closed positions as described above in relation to the hinge structure 120. Needle shield hinge 133 may be formed by molding together thin sections of the leg portion 122 and needle shield 110. Alternatively, a pin (not shown) may be used to form hinge 133. Pivoting of the needle shield 110 about needle hinge 133 occurs freely by moving the needle shield 110 to any desired position or angle.

The dual hinge functionality of the needle guard 100 is unique. The hinge structure 120 provides the first hinge function in the needle guard 100 by permitting pivotal movement of the needle shield 110 in relation to the mounting base 140. This first hinge function is relied upon during and after injection of a medicament into a human or animal patient by the user of the needle guard 100 and prevents accidental contact of the patient and the user with the needle. The second hinge function in the needle guard 100 is provided by needle hinge 133 and allows for movement of the needle shield 110 to a more desirable position during packaging or storage prior to use of the needle guard 100. With reference to FIGS. 1 and 2, a first hinge 150 may be located between the press member 125 and the spring plate 127. A second hinge 152 may be located between the spring member 124 and the base 140. A needle shield hinge 133 may be also referred to as a third hinge member which may be positioned between the guard 100 and the leg 122. A fourth hinge 154 may be located between the toggle joint knee 123 and the toggle joint 121.

The mounting base 140 comprises a needle hub bore 141 extending through the mounting base 140 for securely fitting to and mating with a needle 200 or a needle hub 210 such that the needle extends distally from the mounting base 140. The inner surface of the needle hub bore 141 has a size and shape corresponding to the outer surface of the needle 200 or needle hub 210 to achieve a secure fit and avoid movement of the needle. The needle hub bore 141 may be a conically shaped hole with a diameter that narrows in the same direction as the extension of the needle. Alternatively, the needle hub bore 141 may be provided with longitudinal recesses that correspond and mate with the longitudinal protrusions of standard needle hubs. The mounting base 140 is not movable in relation to a needle 200 arranged on the mounting base 140.

Use of the needle guard 100 may involve the following steps:
(a) the pre-mounted needle 200 and syringe 220 on needle guard 100 is removed from its packaging and the shield 110 is pivoted back about hinge 133 until the spring plate 127 snaps into aperture 129 to hold the shield 110 in an open position;
(b) the user fills the syringe with medicament then penetrates the skin of a patient with the needle;
(c) the user applies pressure to press member 125 with their finger to pivot the needle shield 110 from the open position, pass the dead-center position, and into contact with the skin of the patient;
(d) the user injects the medicament through the needle; and
(e) the user withdraws the needle from the patient whereby the needle shield 110 automatically enters the closed position to enclose and protect the needle within slot 115.

The needle guard 100 may be made of a thermoplastic, plastic or polymeric material such as polypropylene (PP), high-density polyethylene (HDPE), polyamide (PA) and acrylnitrile-butadiene-styrene copolymer (ABS). These materials allow for manufacturing the needle guard 100 as a monolithically formed single article which minimizes manufacturing costs. The thermoplastic, plastic or polymeric material will be selected to achieve sufficient tenacity, rigidity, fatigue resistance, elasticity, and creep deformation resistance in the needle guard 100. Manufacturing of the needle guard 100 comprises the steps of providing a thermoplastic, plastic or polymeric material as starting material for needle guard 100 and molding or injection molding the thermoplastic, plastic or polymeric material into one monolithically formed needle guard 100. The advantages of using a thermoplastic, plastic or polymeric material for construction of the needle guard 100 in comparison to metal include the increased convenience of molding a plastic, the ability to color code a plastic needle guard according to the needle size, and the higher chemical inertness and resistance to corrosion.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A needle guard for protecting a human or animal from accidental contact with a needle connected to said needle guard, comprising:
    a mounting base configured for the needle; and
    a first hinge structure including a spring member and a spring plate that is configured to pivot relative to a needle shield, a second hinge structure connecting the mounting base to the spring member, a third hinge structure connecting a the needle shield to the spring plate, the spring plate being adapted to pivot the needle shield relative to the mounting base from an open position, in which the needle shield is separated from the needle, to a second position in which the needle shield advances towards enclosing the needle;
    wherein the needle shield includes an outer surface having an aperture for receiving the spring plate;
    wherein the third hinge structure is located adjacent to the needle shield, the third hinge structure being adapted to pivot the needle shield relative to the first hinge structure;
    wherein the second hinge structure is located between the mounting base and the first hinge structure; and
    wherein the first hinge structure is located between the needle shield and the second hinge structure.

2. The needle guard according to claim 1, wherein the spring plate is connected to the spring member for cooperating with the needle shield during use with the needle.

3. The needle guard as claimed in claim 1, wherein the spring member is V-shaped and comprises a press member that extends outwardly from the spring member.

4. The needle guard as claimed in claim 1, further comprising:
    a fourth hinge structure including:
        a toggle joint adjacent to the mounting base;
        a leg portion adjacent to the third hinge structure; and
        a toggle joint knee located between the toggle joint and the leg portion.

5. The needle guard as claimed in claim 4, wherein the fourth hinge structure is formed by molding together thin sections of the leg portion and needle shield.

6. The needle guard as claimed in claim 1, wherein the mounting base comprises a needle hub bore for receiving a needle hub connected to the needle.

7. The needle guard as claimed in claim 1, wherein the needle shield comprises a needle lock for securely engaging the needle.

8. The needle guard as claimed in claim 1, being monolithically formed as a single article when manufactured.

9. The needle guard as claimed in claim 1, being made of a thermoplastic, plastic, or polymeric material.

* * * * *